(12) United States Patent  (10) Patent No.: US 8,284,389 B2
Forrer et al.  (45) Date of Patent: Oct. 9, 2012

(54) REFRACTOMETER

(75) Inventors: Christian Forrer, Elsau (CH); Erwin Bossart, Flawil (CH); Félix Bécheiraz, Marthalen (CH)

(73) Assignee: Mettler-Toledo AG, Greifensee (CH)

( * ) Notice: Subject to any disclaimer, the term of this patent is extended or adjusted under 35 U.S.C. 154(b) by 141 days.

(21) Appl. No.: 12/823,401

(22) Filed: Jun. 25, 2010

(65) Prior Publication Data

US 2010/0328652 A1 Dec. 30, 2010

(30) Foreign Application Priority Data

Jun. 26, 2009 (EP) .................................. 09163868

(51) Int. Cl.
*G01N 21/41* (2006.01)
(52) U.S. Cl. ....................................... 356/128; 356/246
(58) Field of Classification Search .......... 356/128–137, 356/244–246
See application file for complete search history.

(56) References Cited

U.S. PATENT DOCUMENTS

| 2,601,128 | A |   | 6/1952 | Rosenthal et al. |
| 3,628,867 | A | * | 12/1971 | Brady ........................... 356/136 |
| 4,126,393 | A | * | 11/1978 | Sumikama et al. ........... 356/130 |
| 4,640,616 | A | * | 2/1987 | Michalik ....................... 356/136 |
| 7,074,364 | B2 |   | 7/2006 | Jähn et al. |
| 7,369,221 | B2 | * | 5/2008 | Amamiya et al. ............. 356/135 |
| 2007/0207554 | A1 | * | 9/2007 | Lin et al. ....................... 436/514 |

FOREIGN PATENT DOCUMENTS

DE 19922285 A1 11/2000
DE 102005038252 A1 2/2007

* cited by examiner

*Primary Examiner* — Hoa Pham
(74) *Attorney, Agent, or Firm* — Standley Law Group LLP

(57) ABSTRACT

A refractometer has a housing (1), a measurement cell (8) arranged in the housing (1), and a lid unit (2). The lid unit has a base plate (3) with a cutout (7) allowing access to the measurement cell, and a lid (4) for covering the measurement cell. The lid is connected to the base plate by way of a hinge. The lid unit also has a lid insert (11, 17, 18, 28, 31, 35, 39) that is arranged replaceably in the lid. The lid unit (2) is detachably connected to the housing by means of a connecting element that is itself connected to the base plate.

19 Claims, 4 Drawing Sheets

REFRACTOMETER

CROSS-REFERENCE TO RELATED APPLICATIONS

This application is entitled to, and claims benefit of, a right of priority under 35 USC §119 from European patent application 09 16 3868.4, which was filed 26 Jun. 2009. The content of the European application is incorporated by reference as if fully recited herein.

TECHNICAL FIELD

The invention relates to a refractometer, and particularly to a lid unit for a refractometer, which is connected detachably therewith and has a replaceable lid insert.

BACKGROUND OF THE ART

Refractometers are used to determine refractivity, or a refractive index, refractometry being recognised as a standard method of chemical analysis. The refractive index is a value that is unique for any given substance, so according to the applicable standards in this field of analysis, it must be possible to clean any parts of the refractometer that come into contact with the sample easily and thoroughly.

Commercially available devices, such as the RE 40 refractometer produced by Mettler-Toledo, usually include a housing that comprises the measurement optics and the measurement cell, the cell being loaded with the sample for measurement. The measurement optics are arranged in the device in such manner that a beam of light transmitted from a radiation source can be coupled into and out of the measurement cell. The output coupled light coming from the measurement cell after interacting with the sample substance is detected using a suitable detection device. In this context, the word light is used synonymously with radiation. Typically, the refractive index n is measured on the sodium D line, that is to say at a wavelength of 589.3 nm, but other temperatures or wavelengths can also be used. The refractive index is affected by temperature, and is usually measured at 25° C. or this temperature is used as a reference therefor. Accordingly, many refractometers are equipped with a heater for warming the sample up.

The measurement cell is closed off from the outside by a lid, which is usually attached permanently to the device, and only the surface thereof can be cleaned without significant effort. Especially if the same refractometer is to be used for different sample substances, it would be advantageous if it were possible to clean the lid easily and thoroughly to avoid contaminating a sample substance with residues of old samples.

An unmet object of the prior art is thus to provide a refractometer with an improved lid unit that enables the lid unit to be cleaned quickly and easily.

SUMMARY

This unmet object is met by a refractometer having a housing, measurement cell arranged therein and a lid unit, which comprises a base plate having a cutout allowing access to the measurement cell of the refractometer, a lid that is connected to the base plate by a hinge, and a lid insert for covering the measurement cell, this lid insert being arranged in the lid so as to be replaceable. The lid unit is also detachably connected to the housing via a connecting element that is connected to the base plate.

The connecting element enables the lid unit to be removed easily from the refractometer and cleaned separately. The lid unit may thus be detached from the housing very easily, preferably without the use of any tools, thus avoiding the possibility that, for example, a relatively aggressive cleaning solution might attack the area directly surrounding the measurement cell during cleaning. The modular construction of the lid unit enables it to be cleaned easily, and at the same time it helps to prevent the measurement cell and/or the housing from being damaged during the cleaning operation.

The replaceable lid insert also enables the sample to be conditioned while it is in the measurement cell. In this way, samples may be analysed under very different conditions, and very different samples may be analysed using the same refractometer simply by replacing the lid insert.

In another embodiment, the lid insert and/or the lid unit may be designed for one-time use, that is to say as consumable material, which is particularly advantageous for measurements to be carried out in sterile conditions.

The base plate of the lid unit is furnished with a cutout to allow access to the measurement cell, so that the measurement cell may be charged in the measurement device even while the lid unit is attached. The cutout may be closed by the lid, particularly by the lid insert.

In a further embodiment, the lid unit is also equipped with at least one sealing element, which isolates the base plate from the measurement cell. This may be arranged around the periphery of the cutout, and may be an O-ring, for example. The sealing element may serve to prevent substances from getting between the measuring device and the base plate of the lid unit by closing up a possible gap.

The base plate may also be furnished with a lip running round the cutout, the dimension and alignment of which should be adapted to the design of the measurement cell. For example, this lip may protrude into the measurement call or be directed away from the measurement cell, so that any substance residues remaining on the base plate after filling are not able to penetrate as far as the measurement cell.

The hinge may also include two linked parts, so that the lid and the base plate may be separated from one another. In this way, for example, any substance residues that have accumulated on the lid or in the hinge may be removed easily and thoroughly. Moreover, at least some components of the lid unit, for example the base plate, may be cleaned not only by hand, but also by machine, in a dishwasher for example. The hinge may for example include two parts connected via a pin that is removable by hand, or two parts that are joined via a snap-on or latching connection.

In a further embodiment, the lid is designed such that when it is open or closed it is retained in its respective position, for example by the provision of a closing element, for example a magnet, close to the handle, and of a resetting element, for example a spring, in the hinge. The force of the closing element is adjusted to match the force of the resetting element, such that the lid may only be moved from either position to the other by the application of additional force.

The lid insert is preferably connected detachably to the lid, for example via a snap-fit connection, so that the lid insert may be replaced without the use of tools. The replaceable lid insert may be provided in a wide variety of designs.

The lid insert may be configured as a pressing insert, as a means for spreading the sample evenly in the measurement cell. The pressing insert may include a stamp with which pressure is applied to a sample in the measurement cell, thereby improving the contact between the sample and a measurement unit arranged in the housing, for example by distributing the sample in a flat manner over the active measurement surface. This is particularly advantageous in the case of highly viscous substances, especially if the measurement unit is an optical measurement unit that interacts with a sample located in the measurement cell via a window in the bottom or wall of the measurement cell. The pressing insert is arranged in the lid in such manner that it applies pressure to the sample when the lid is closed, spreading the sample evenly in the measurement cell. In so doing, the pressing insert may displace the sample partially.

The lid insert may also be configured as an optical shield that shields the measurement cell from external light. For example, a plate or panel with a dark surface that covers the cutout when the lid is closed is suitable for use as an optical shield. This embodiment is advantageous when an optical measurement unit is used, since it serves to prevent errors in the measurement result caused by ambient or external light.

The lid insert may also be designed as a sealing insert, and insulate the measurement cell from the outside. Such a sealing insert may be designed in such manner that it seals the measurement cell off when the lid is closed, and serves to prevent volatile substances from evaporating.

The lid insert may also be designed as a temperature control medium for controlling the temperature of the sample, such that the sample may be cooled or heated. The temperature control medium may be arranged in the lid insert or connected thereto, wherein the lid insert should be made from a material that conducts heat. An example of a temperature controlling medium integrated in the lid insert would be one or more Peltier elements that may be used for heat and cooling, or a resistance heater. The lid insert may also be connected to an external temperature controlling device, such as a thermostat or cryostat, via suitable wires or connectors. In this way, the temperature controlling unit often located in the refractometer may be assisted, in order to shorten the time required for controlling the temperature of the measurement cell, and it may also help to simplify sample preparation by liquefying a highly viscous or solid sample directly in the measurement cell, which is advantageous both for the measurement and for the subsequent cleaning.

The lid insert may also be designed as a medium for modifying the pressure in the measurement cell, such that for example a suitable pump may be used to increase the pressure in the measurement cell and on a sample arranged therein via suitable feeds, or to create a vacuum in the measurement cell. With a vacuum, for example, air bubbles may be removed from the sample, or vented. Changing the pressure may serve as a means to influence the flowability of the sample, by rendering it more solid or more liquid, for example.

The lid insert may also be designed as a means for charging the measurement cell with a gas. The gas used may either be an inert gas, such as helium, nitrogen or argon, or a gas-phase reagent that is able to react with the sample. In this way, a reaction between the sample and the ambient atmosphere, such as oxidation or reduction, may be either prevented or deliberately initiated. The gas may be introduced through suitable feeds in the lid insert.

The lid unit may also include a sensor for recording a physical and/or chemical property of the sample, for example an optical transmittance unit that is able to capture inclusions or also record spectra, or equally analytical sensors such as pH sensors, conductivity sensors, or other sensors. In this way, the refractometer may be used to determine a further property of the sample as well as its refractive index. The sensor is preferably a part of the lid insert.

The base plate may be furnished with a lip running round the periphery thereof, and which helps to prevent liquid from spilling, so that substances are prevented from getting onto the measurement device itself or dripping down the outside surfaces thereof.

This lip may also be furnished with at least one drain, for example in the form of a cutout or channel in the lip, so that excess sample material is transported away from the measurement cell and is able to drain off at a defined point.

The base plate of the lid unit may also have a surface that is as smooth as possible or even coated, so that substance residues are not able to accumulate thereon.

Various polymers, metals or metal compounds are particularly suitable for use as the material for the lid unit base plate. The material should be resistant to the substances and cleaning agents used, it should also be durable and scratch-resistant so that no depressions or grooves develop in the base plate during use. Suitable materials include stainless steel, acid-resistant steel, other high-grade steels as well as polytetrafluoroethylene (PTFE) and other chemically resistant plastics or polymers, and other materials.

In a further embodiment, the base plate also includes a functional surface coating, for example a PTFE coating, a high grade steel coating or a nanocoating. The coating is selected such that it supports or improves the stated specifications for the material. In this way, the base plate may be designed so as to be particularly easy to clean, and deposits of the sample of the base plate may be minimised or even prevented entirely thereby.

The connecting element for connecting the base plate with the housing may be a part of a magnetic connection, a snap-fit connection or a bayonet connection, and of course other connections that are separable without tools may also be used. For example, a magnetic connection may consist of two attracting magnets, or one magnet and an element made from a magnetisable metal such as iron. In this context, a first connecting element is affixed to the housing and a second is affixed to the base plate. The strength of the connection between the two connecting elements is preferably designed such that the lid unit may be separated from the housing by hand but is not easily movable.

Depending on the design of the lid unit, particularly its size and weight, the base plate may include one or more first connecting elements that cooperate with the same number of second connecting elements on the housing to secure the lid unit. The base plate and/or the surface of the measurement device may also be furnished with a flat connecting element, or it may be designed as such and may cooperate with one or more matching parts on the measurement device or base plate.

Of course, it is also possible to use a lid unit that is equipped with lid inserts having two or more of the means or designs described in the preceding.

BRIEF DESCRIPTION OF THE DRAWINGS

Various designs of a lid unit for a refractometer meeting the present objectives will be described in the following with reference to the drawings, in which identical parts are identified with identical reference numbers and in which.

DETAILED DESCRIPTION OF A PREFERRED EMBODIMENT

Figure 1:
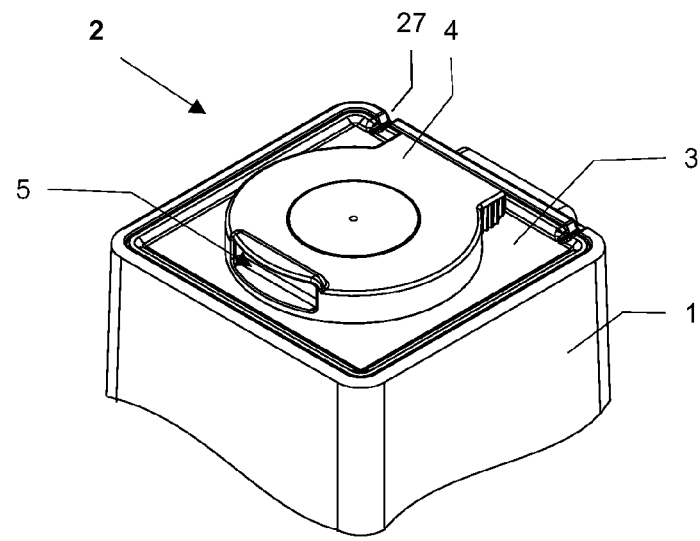
FIG. 1 is a partial perspective view of a refractometer with a closed lid unit.

FIG. 1 is a three-dimensional representation of a refractometer, also referred to in the following as a measurement device, including a housing 1, a lid unit 2, which has a base plate 3 and a lid 4, which is closed in this representation. Lid 4 is furnished with a handle 5 for opening and closing lid 4.

Figure 2:
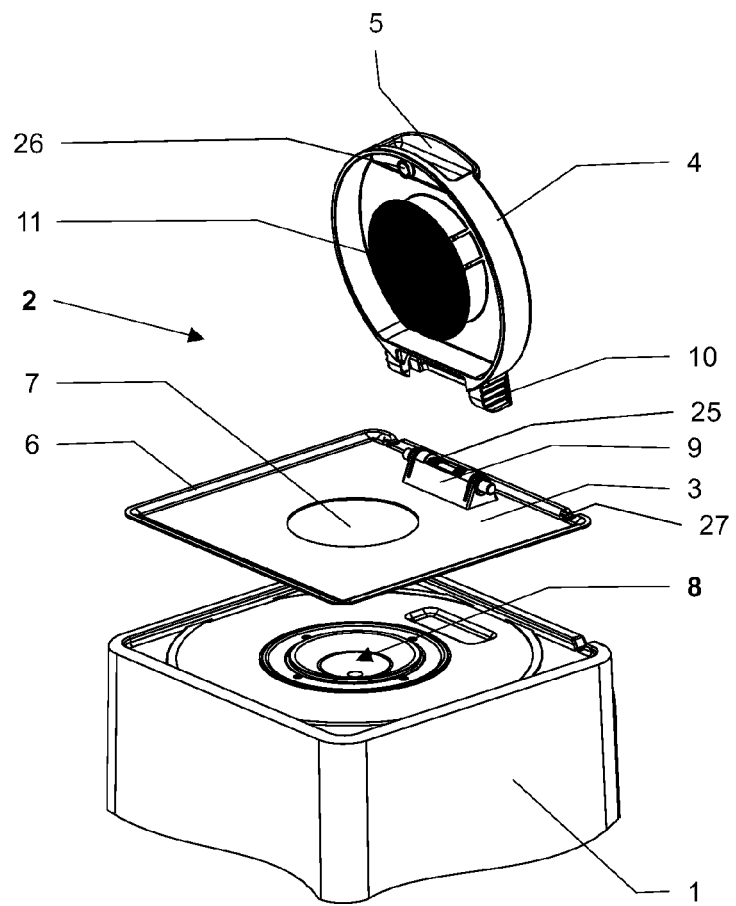
FIG. 2 is a partial exploded perspective view of the FIG. 1 refractometer and lid unit with the lid in an open position.

In FIG. 2, lid unit 2 and the measurement device have been separated from one another and are shown in an exploded diagram. Base plate 3 has a peripheral lip 6 and a cutout 7 through which a measurement cell 8 situated in the measurement device, or more precisely in housing 1, may be charged with a sample when lid unit 2 is mounted and lid 4 is open. Two drain channels 27 are arranged in lip 6 so that excess sample material may drain away from base plate 3. The refractometer comprises a funnel-shaped measurement cell 8. Below measurement cell 8 in the measurement device there is an optical measurement unit that may be used to determine the refractive index of a sample placed in measurement cell 8. The bottom of measurement cell 8 is configured as an optical window and the optical measurement unit is arranged directly adjacent thereto. Alternatively, at least one optical window might be arranged in the wall of measurement cell 8.

Additionally, a first hinge part 9 is attached to base plate 3, and together with a second hinge part 10 arranged on lid 4, it forms a movable hinge. Hinge parts 9, 10 are constructed in such manner that they may easily be joined to one another or separated by hand.

The combination of a torsion spring 25 located in the hinge and a magnet 26 located in handle 5 and directed towards the base plate is particularly user-friendly, and ensures that when in the open position lid 4 is not able to close under its own weight. Magnet 26 also ensures that the lid remains in the closed condition. The spring force of torsion spring 25 and the magnetic force of magnet 26 are synchronised in such manner that lid 4 remains in the selected position—open or closed—without the application of additional force.

An optical cover 11 with a dark surface is shown on the side of lid 4 facing measurement cell 8. When lid 4 is closed, this cover 11 is positioned over cutout 7, thereby shielding measurement cell 8 from any external light that might penetrate from the outside, even if lid 4 is not lying completely flat on base plate 3.

FIGS. 3 to 9 show cross-sections of a number of embodiments of a closed lid unit 2 with various lid inserts, wherein only sections of the measurement device and lid unit 2 are shown in each case.

When lid unit 2 is connected to the measurement device, base plate 3 lies flush on top of the measurement device. Lip 6 extending round base plate 3 is curved slightly upwards so that base plate 3 forms a collecting tray for any substance that drips from the measurement cell or any of the substance that escapes due to incorrect charging. In this case, base plate 3 contains a magnetic material, so that it is attracted by plate- or disc-shaped magnets 12 arranged on or near the surface of housing 1, and thus holds lid unit 2 immobile on housing 1 of the refractometer. Lid 4 is essentially hollow, and besides handle 5 and second hinge part 10 is equipped with an end- or covering plate 13 that is surrounded by a peripheral lip 14.

A first mounting 15 is provided inside lid 4, protruding into lid 4, and the free end thereof is provided with a first connecting element 16, which in this case is in the shape of a disc. As is shown in all of FIGS. 3 to 9, a lid insert 17, 18, 28, 31, 35, 39 may be attached to this first connecting element 16 without tools.

For this purpose, connecting element 16 is constructed as a plastic disc, and the various lid inserts 18, 28, 31, 35, 39 may be placed over it. A certain amount of play is built into the connection between lid insert 17, 18, 28, 31, 35, 39 and connecting element 16, so that the depth to which lid insert 17, 18, 28, 31, 35, 39 protrudes into measurement cell 8 is influenced not only by the dead weight of lid insert 17, 18, 28, 31, 35, 39 but also by the sample, for example its viscosity or volume, thus making it possible to prevent lid insert 17, 18, 28, 31, 35, 39 from damaging measurement cell 8.

The cutout (see also FIG. 2) in base plate 2 functions as an access to measurement cell 8, which in this case is in the shape of a funnel. A window 19 is provided in the bottom of measurement cell 8, and separates measurement cell 8 from measurement unit 20 arranged below it.

Figure 3:
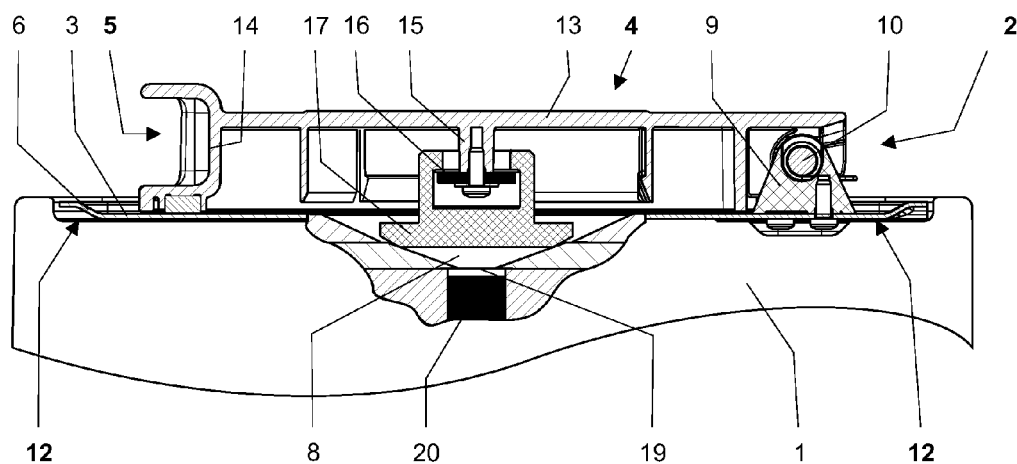
FIG. 3 is a cross-section view through part of a refractometer with a lid unit that is furnished with a sealing insert.

Sealing insert 17 is constructed in the shape of a mushroom and, as shown in FIG. 3, protrudes into measurement cell 8 when lid 4 is closed, sealing the cell off from the outside as the head of sealing insert 17 lies flush with the side walls of measurement cell 8 under its own deadweight. Sealing insert 17 also shields the measurement cell from external light.

Figure 4:
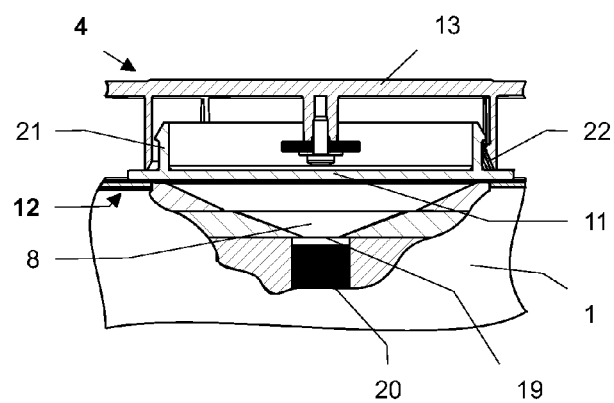
FIG. 4 is a cross-section view through part of a refractometer with a lid unit that is furnished with an optical cover.

FIG. 4 shows lid unit 2 with optical cover 11 as a lid insert. Optical cover 11 is essentially a flat disc having a dark surface (see FIG. 2), which shields measurement cell 8 from external light when lid 4 is closed. The side of this flat disc on the opposite side to the dark surface is furnished with at least two hooks 21, which are able to engage in correspondingly shaped second connecting elements 22 on lid 4, so that optical cover 11 may be attached to lid 4 via a detachable snap-on connection. The snap-on connection is designed in such manner that optical cover 4 may be inserted in lid 4 without the use of tools.

Figure 5:
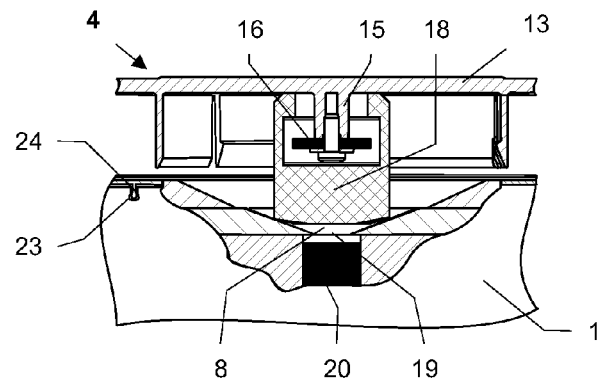
FIG. 5 is a cross-section through part of a refractometer with a lid unit that is furnished with a pressing insert.

FIG. 5 shows a further embodiment of the lid insert configured as a pressing insert 18 that may be attached to lid 4 via first connecting element 16. Pressing insert 18 is constructed in such manner that it protrudes into measurement cell 8 when lid 4 is closed and presses a sample against window 8. The size of pressing insert 18 is such that when lid 4 is closed, its one end is pressed against lid 4 and the other end is pressed the side walls of measurement cell 8 in order to exert pressure on a sample in measurement cell 8.

Lid inserts 11, 17, 18, 28, 31, 35, 39 are attached to the lid with a small amount of play so that they may be pressed onto or into measurement cell 8 when lid 4 is closed, thereby closing measurement cell 8, or more precisely the sample located therein, more accurately.

FIG. 5 also shows a snap-on connection between base plate 3 and housing 1 of the measurement device for exemplary purposes. This connection may be created by at least one recess 23 in the surface of housing 1 and at least one matching protrusion 24 in base plate 3, or equally by raised areas on housing 1 and matching engaging means on base plate 3.

Additional lid inserts are shown in FIGS. 6 to 9 in significantly simpler form and without connecting elements 16.

Figure 6:
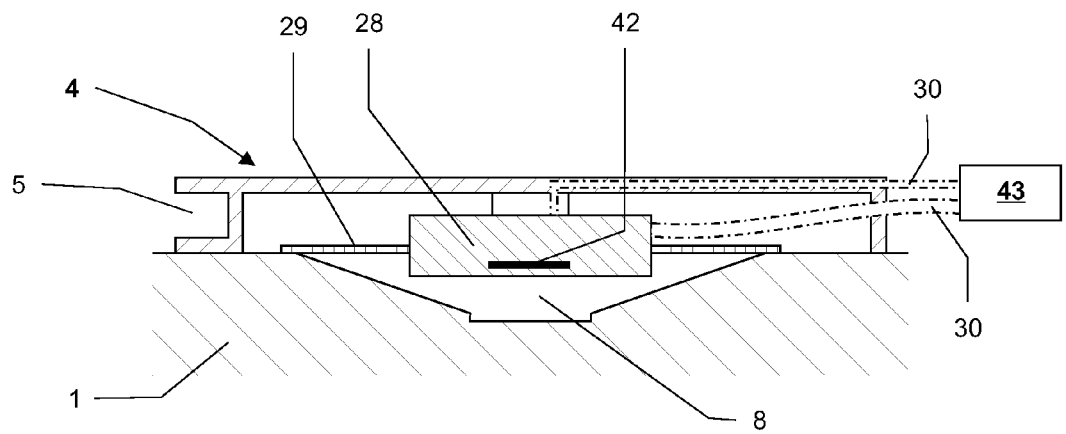
FIG. 6 is a cross-section view through part of a refractometer with a lid unit that is furnished with a temperature controlling means.

FIG. 6 shows a lid 4 having a lid insert 28 which is furnished with an internal or external temperature controlling means 42, 43. Lid insert 28 also comprises a cover 29 that optically shields measurement cell 8. In FIG. 6, both an external temperature control means 43 and an internal temperature control means 42 are indicated, although the lid unit is only able to accommodate one of these at a time.

Internal temperature controlling means 42 may be for example resistance heaters and Peltier elements. Peltier elements may be used both the heating and cooling. Lid insert 28 may also be connected to an external temperature controlling means 43, such as a thermostat or cryostat, as is indicated by wires 30, which represent possible variants for routing the wires. Depending on the design of temperature controlling means 42, 43, lines 30 may also be electrical wires, which supply energy to internal temperature controlling means 42, for example.

Figure 7:
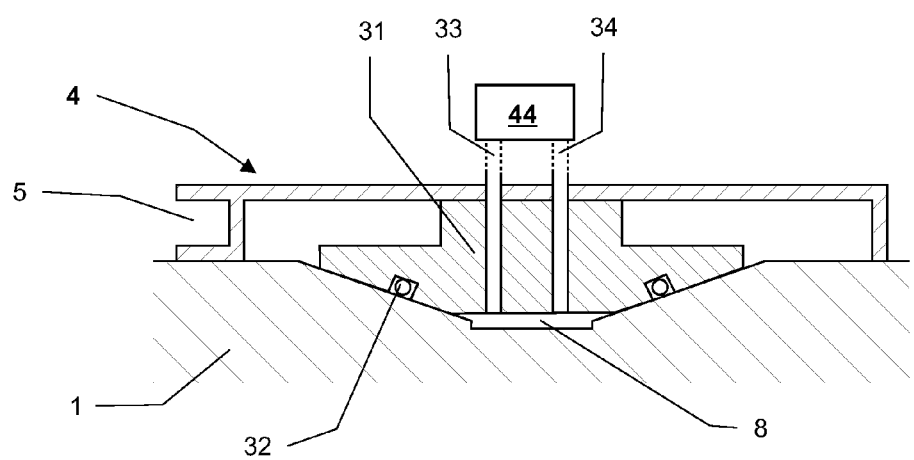
FIG. 7 is a cross-section view through part of a refractometer with a lid unit that is furnished with means for altering the pressure in the measurement cell.

FIG. 7 shows a further lid insert 31, which may be sealed off from measurement cell 8 via at least one sealing element 32. Lid insert 31 also has an inlet line 33 and an outlet line 34 via which a gas may be fed into measurement cell 8 or a vacuum may be created, as is indicated by a unit 44 containing a pump and/or gas reservoir.

Figure 8:
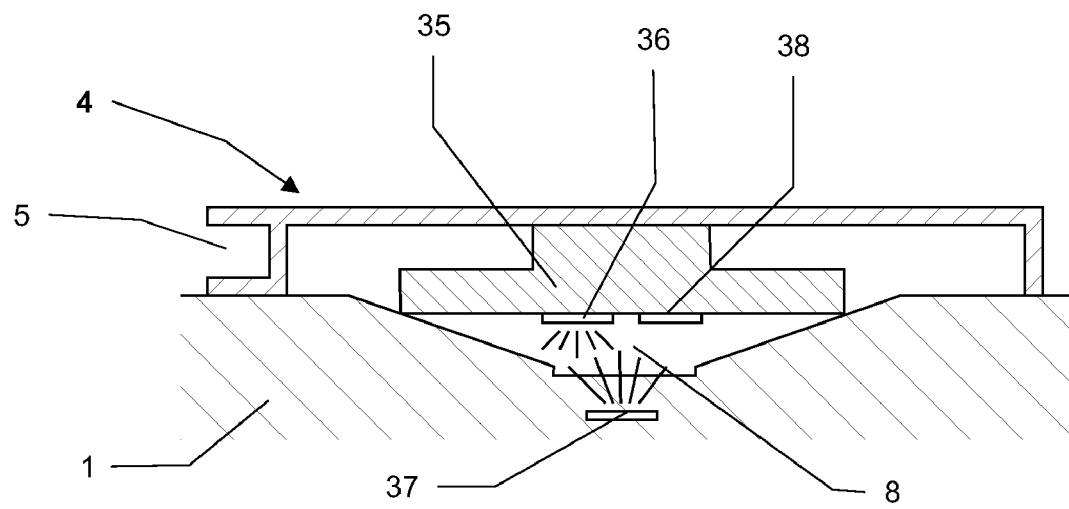
FIG. 8 is a cross-section view through part of a refractometer with a lid unit that is furnished with an optical sensor unit.

A lid insert 35 according to FIG. 8 shields measurement cell 8 from external light and is also equipped with at least one light source 36, 37 and a sensor 38. The homogeneity of the sample may be tested in incident or transmitted light with this arrangement, and other optical measurements may be conducted on the sample, such as recording spectra. It is further possible to capture a transmitted light or incident light image of the sample and check the image for air bubbles, suspended particles, or inclusions. This text may be carried out visually by the user on the basis of the images and/or spectra recorded, or by the device software using a suitable evaluation routine.

Figure 9:
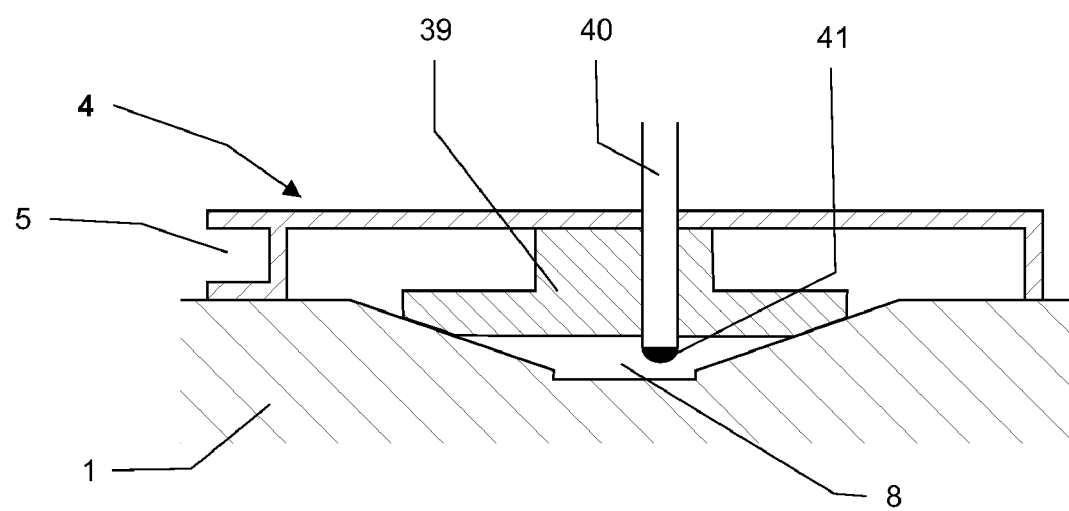
FIG. 9 is a cross-section view through part of a refractometer with a lid unit that is furnished with an analytical sensor.

FIG. 9 shows a lid insert 39 having a sensor 40 that is arranged so that its sensitive element 41 is able to come into contact with a sample in measurement cell 8. Suitable sensors may be all kinds of analytical sensors, such as electrochemical or electrophysical sensors. These include for example ion-sensitive, amperometric or potentiometric sensors such as pH, oxygen or conductivity sensors.

Although the invention has been described with reference to representations of specific embodiments, it is evident that many other design variations may be created on the basis of the teaching of the present invention, for example by combining features of the individual embodiments with each other and/or by substituting individual functional units of the embodiments.

The invention claimed is:

1. A refractometer, comprising:
   a housing;
   a measurement cell, arranged in the housing, in which is received a sample to be measured; and
   a lid unit, the lid unit comprising:
      a base plate, a cutout therein allowing access to the measurement cell of the refractometer;
      a lid for covering the measurement cell;
      means for hingedly connecting the lid to the base plate; and
      a lid insert, replaceably arranged in the lid; and
      a connecting element that detachably connects the lid unit to the housing by connecting the housing to the base plate.

2. The refractometer of claim 1, wherein:
   the means for hingedly connecting comprises two parts that are coupled to one another so the lid separates from the base plate.

3. The refractometer of claim 2, further comprising:
   an optical shield that prevents external light from penetrating the measurement cell, the optical shield comprising at least a part of the lid insert.

4. The refractometer of claim 3, further comprising:
   a pressing insert that spreads a sample in the measurement cell, the pressing insert comprising at least a part of the lid insert.

5. The refractometer of claim 3, further comprising:
   a sealing insert that insulates the measurement cell from the outside environment, the sealing insert comprising at least a part of the lid insert.

6. The refractometer of claim 2, wherein:
   the connecting element comprises a magnetic connection.

7. The refractometer of claim 2, wherein:
   the connecting element comprises a snap-on connection.

8. The refractometer of claim 2, wherein:
   the connecting element comprises a bayonet fastening.

9. The refractometer of claim 1, further comprising:
   a means for controlling temperature, comprising at least a part of the lid insert.

10. The refractometer of claim 1, further comprising:
    a means for changing the pressure in the measurement cell, comprising at least a part of the lid insert.

11. The refractometer of claim 1, further comprising:
    a means for charging the measurement cell with a gas, comprising at least a part of the lid insert.

12. The refractometer of claim 1, further comprising:
    a sensor for recording a physical and/or chemical property of a sample.

13. The refractometer of claim 1, further comprising:
    a lip which extends peripherally as a part of the base plate.

14. The refractometer of claim 13, further comprising:
    a drain channel on the peripherally extending lip.

15. The refractometer of claim 1, wherein:
    the base plate comprises, or at least has a surface coating that comprises, a chemically resistant material.

16. The refractometer of claim 1, further comprising:
    an optical shield that prevents external light from penetrating the measurement cell, the optical shield comprising at least a part of the lid insert.

17. The refractometer of claim 1, further comprising:
    a pressing insert that spreads a sample in the measurement cell, the pressing insert comprising at least a part of the lid insert.

18. The refractometer of claim 1, further comprising:
    a sealing insert that insulates the measurement cell from the outside environment, the sealing insert comprising at least a part of the lid insert.

19. A lid unit, connected to a refractometer housing in which a measurement cell is arranged, comprising:
    a base plate, a cutout therein providing access to the measurement cell;
    a lid for covering the measurement cell;
    means for hingedly connecting the lid to the base plate; and
    a lid insert, replaceably arranged in the lid.

* * * * *